United States Patent [19]

Jones

[11] Patent Number: 4,755,287
[45] Date of Patent: Jul. 5, 1988

[54] FIVE STAGE INTERNAL CELL SEPARATOR

[76] Inventor: Wendy L. Jones, Box 376, 111 2nd Ave., N.W., Arlington, Minn. 55307

[21] Appl. No.: 37,269

[22] Filed: Apr. 10, 1987

[30] Foreign Application Priority Data

Sep. 10, 1986 [CA] Canada ............................ 517923

[51] Int. Cl.4 .................................. B07B 1/04
[52] U.S. Cl. ................................ 209/355; 209/235
[58] Field of Search ............... 209/235, 353, 355, 250

[56] References Cited

U.S. PATENT DOCUMENTS 1,430,636 10/1922 Fergeson ................... 209/355 X
3,386,580 6/1968 Grabweczyk ............... 209/355 X Primary Examiner—A. Michael Chambers
Assistant Examiner—John C. Fox
Attorney, Agent, or Firm—George H. Dunsmuir

[57] ABSTRACT

Cells are normally separated by velocity sedimentation and/or density gradient centrifugation, counter current distribution or selective agglutination. The cells may also be separated using a multi-sectioned plastic sleeve defined by a plurality of plastic cylinders with screens and O-rings therebetween and a retaining plate at the top end of the cylinders. These methods present various problems including a large variation in the sizes of cells isolated in any fraction, high costs of materials, and/or exposure of the cells to air immediately following separation. These problems are overcome by means of a simple cell separator which permits separation on the basis of size, and which is sealed maintaining a sterile environment during the separation process. The separator includes an elongated, tubular casing with an open upper end and a closed lower end, an elongated, tubular column for insertion into the casing, the column having a closed upper end and an open lower end, the column including a plurality of separate interconnectable tubular sections for releasably supporting cup-shaped filters between adjacent sections, and a flange on the uppermost section for sealing engagement with the upper end of the casing. Cells in a liquid medium are introduced into the column through an inlet duct in the close upper end of the column. The cells are separated by means of the filters, and the liquid medium is discharged through an outlet duct in the lower end of the casing. Thus, the column can be inserted and removed from the casing as a unit, and disassembled from the upper or lower end thereof.

8 Claims, 1 Drawing Sheet

FIVE STAGE INTERNAL CELL SEPARATOR

BACKGROUND OF THE INVENTION

This invention relates to a separator, and in particular to a cell separator for separating various cells on the basis of size.

There are several popular methods of separating or sorting cells, including (a) velocity sedimentation and/or density gradient centrifugation, (b) counter current distribution, and (c) selective agglutination.

Velocity sedimentation and density gradient centrifugation both rely upon the density (rather than size differences) of the cells or particles being separated. The density of the cells dictate the rates at which the cells drift through a substance of known density and viscosity during centrifuging. It has been found that the use of this method results in a significant variation in the sizes of the cells or particles isolated in any single collected fraction.

Counter current distribution relies upon lipid related membrance differences between cells. Such differences cause the cells to be more attracted to a positively or negatively charged medium. The method involves the use of two liquids, namely dextran solution and a polyethylene glycol solution. At present, there is no complete understanding of the biological significance or implication of separating cells on the basis of electrical charge. After sorting, the cells must be subjected to treatment with antibiotics. In certain cases, cell contact with antibiotics is undesirable.

In selective agglutination, ligens are bound to specific cell surface sugars. Cells sorted using this mehtod are either precipitated from solution or are attached to a ligen bound to a solid support. Only a few types of cells can be sorted using this method. Contact with the ligen must be as brief as possible and, under certain conditions, a ligen may behave as a mitogen which is completely undesirable. The continuous purches of ligen, sugars, equipment and operating medium is costly.

Another method of cell sorting involves the use of a multi-sectioned plastic sleeve defined by a plurality of plastic cylinders with screens and O-rings therebetween, and a retaining plate at the top end of the cylinders. The plate is secured with two wing nuts on long screws situated on each side of the cylinder. Separation medium is loaded into the sleeve from the top and flows through the screens for discharge from the bottom of the unit. The cells are loaded into the top of the sleeve and permitted to settle through screens of successively decreasing size. In order to harvest the cells, the unit must be dismantled from the top down. This method of separation is unsatisfactory for several reasons. During cell separation, the undisrupted flow of liquid is critical. During loading of the column, it is essential that no air remain trapped under any of the screens. Trapped air causes turbulence as liquids flow around these pockets, resulting in an artifactual separation. The particular O-ring plastic sleeve design often permits slight buckling to form in the surface of the screens which trap large bubbles of air. The sleeve is designed to be loaded from the top which often produces sealed chambers when mesh pose size is less than 40 $\mu$m. The mesh size of the screens usually required to separate the various types of cells ranges from 20 $\mu$m to 1 $\mu$m. Sealed chambers occur when the liquid passing from the upper chamber, large mesh screen to a lower chamber wets the complete surface of the subjacent smaller mesh screen. Because of the high surface tension of the liquid between the pores of the mesh or screen, only the upper chambers fill completely leaving partially filled lower chambers. Liquid frequently "wicks" out of the device through the screens, creating large leaks and contamination of the contents of the unit. O-ring popping occurs because of unequal pressure on each side of the sleeve, causing leakage. Because the device must be disassembled from the top down, cells are exposed to air, which causes drying and contamination problems.

The object of the present invention is to solve the above-identified problems by providing a relatively simple cell separator for separating cells on the basis of size which is sealed and sterile during the separation process.

SUMMARY OF THE INVENTION

Accordingly, the present invention relates to a cell separator comprising elongted, tubular casing means, said casing means having an open upper end and a closed lower end; elongated, tubular column means for insertion into said casing means; said column means having a closed upper end and an open lower end, said column means including a plurality of separate, interconnectable tubular sections adapted to releasably support filter means between adjacent sections, and flange means on the uppermost section for sealing engagement with the upper end of said casing means; inlet duct means in said closed upper end of said column means for introducing cells in a liquid medium into said column mmeans; and outlet duct means in said casing means beneath the lower end of said column means for discharging liquid from said casing means, whereby said column means can be inserted into and removed from said casing means as a unit, and disassembled from the upper or lower end thereof.

BRIEF DESCRIPTION OF THE DRAWINGS

The invention will now be described in greater detail with reference to the accompanying drawing, which illustrates a preferred embodiment of the invention, and wherein.

DESCRIPTION OF THE PREFERRED EMBODIMENT(S)

Figure 1:
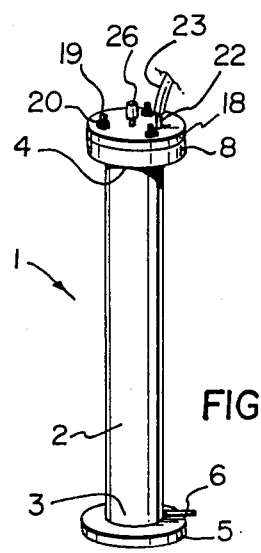
FIG. 1 is a perspective view from one side and above of a cell separator in accordance with the present invention.
Figure 2:
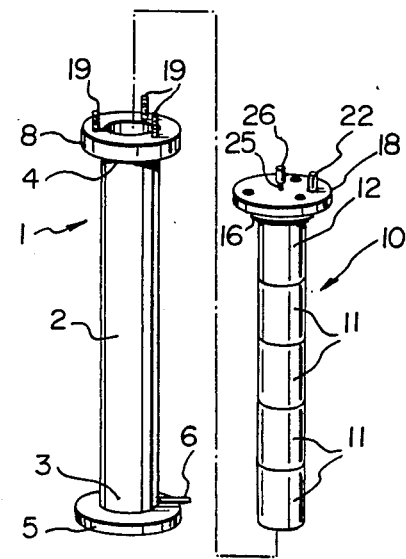
FIG. 2 is an exploded, perspective view from one side and above of the cell separator of FIG. 1.

With reference to the drawing, the preferred embodiment of the cell separator of the present invention includes an elongated tubular casing generally indicated at 1 defined by a cylindrical side wall 2 with a closed bottom end 3 and an open top end 4. A disc-shaped base 5 is attached to the bottom end 3 of the casing 1 for supporting the latter. An outlet duct 6 is provided in the lower downwardly tapering end 7 (FIG. 3) of the side wall 2. An annular flange 8 extends outwardly from the upper end 4 of the side wall 2 for connecting a column generally indicated at 10 to the casing 1.

Figure 3:
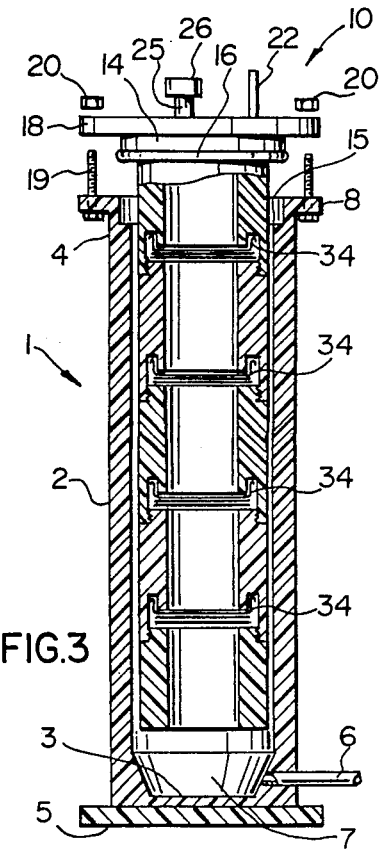
FIG. 3 is a schematic longitudinal sectional view of the cell separator of FIGS. 1 and 2.

Referring to FIG. 3, the column 10 is defined by a plurality of discrete sections 11 and 12. Apart from the last, lower most section, all of the sections 11 are identical to each other, and are therefore interchangeable. The uppermost section 12 includes a shoulder 14 at the top end thereof for seating on a ledge 15 on the top inner end of the casing side wall 2. An O-ring 16 is mounted in a concave groove (not shown) at the bottom edge of the shoulder 14 for forming a seal between the casing 1 and the column 10. The top end of the column section 12 is defined by a cover 18 of larger diameter than the shoulder 14 for mounting on the flange 8 of the casing 1. The column 10 is secured in the casing 1 by bolts 19 and nuts 20. An inlet duct 22 is provided in the cover 18 for connection with a tube 23 through which air, either at atmospheric pressure or lightly pressurized is introduced into the column 10. A tube 25 extends upwardly from the centre of the cover 18, and is externally threaded at its top end for receiving a cap 26. Cells and liquid medium are introduced through this tube. The bottom end of the uppermost section 12 is similar to the remaining column sections 11, with the exception of the last, lower most section, which contains no screw threads.

Figure 4:
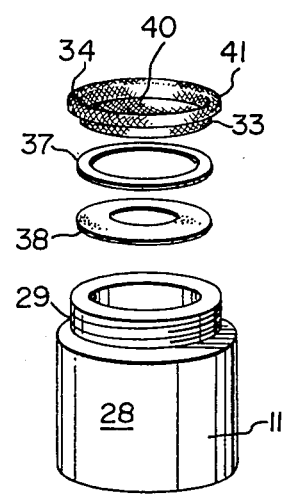
FIG. 4 is an exploded perspective view of a column section and filter for use in the separator of FIGS. 1 to 3.
Figure 5:
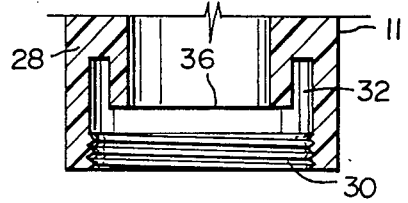
FIG. 5 is a longitudinal sectional view of the bottom end of the column section of FIG. 4.

With reference to FIGS. 4 and 5, each of the column sections 11 includes a hollow cylindrical body 28 with a reduced diameter externally threaded top end 29 and a recessed, internally threaded bottom end 30, with the exception of the lowermost column section 11, so that similar column sections can be connected end-to-end. An internal annular recess 32 is provided above the threaded bottom end 30 of each section 11 and 12 for receiving side wall 33 of a generally cup-shaped filter 34. The recess 32 surrounds the recessed bottom end 36 of the body 28. The filter 34, a nylon retaining ring 37 and a rubber sealing ring or gasket 38 are sandwiched between the top end of one section 11 and the bottom end 36 of the superadjacent section 11 or 12.

The filter 34 is defined by a nylon screen available under the trademark NITEX (H. M. Thompson Company). Each filter 34 includes the side wall 33 and a flat, circular bottom wall 40. This is the shape the filter assumes once fitted into the unit. The top end of the side wall is folded over to define an annular, downwardly extending flange 41. During use, a portion of the side wall 33 and the flange 41 extend upwardly into the annular recess 32. Typically, the screen sizes used for the filters 34 are 500 $\mu$m, 250 $\mu$m, 120 $\mu$m and 40 $\mu$m for plant cells, and 40 $\mu$m, 20 $\mu$m, 15 $\mu$m and 10 $\mu$m for animal cells.

The separator is, of course, autoclavable and will be appreciated that during use, the separator is a completely sealed and sterile unit. Moreover, the joints between adjacent sections of the inner column 10 are sealed. Thus, wetting of the exterior of the column sections is prevented. The cell separating screens or filters 34 are firmly held in place by the nylon retaining ring 37 and the rubber sealing ring 38, which partially seal the junction between adjacent sections 11 and 12 of the column 10. The separator can be operated continuously or intermittently, i.e. with or without continuous liquid input. Liquid can be discharged from the casing 1 under gravity or using sterile air under light pressure, introduced through the central tube 25 in the cover 18.

Following sorting or separation, the cells are retained on the filter 34 in each column section 11 or 12. The surfaces of the filters 34 remain moist, even after the column has been drained which prevents damage to the cells because of drying and reduces the likelihood of direct contact with a contaminated external environment.

While the five-stage cell separator shown in the drawing was designed for use in human tumor cell research, there are many other possible uses of the separator. The separator has been used to sort plant callus in a liquid culture, and has a high potential for use in a variety of disciplines, e.g. for sorting spheroids or other tumor cell lines whose biological activities of which produce size differences within the cell population and the separation of artificially fused hybrid cells from population of non-fused cells in both plant and animal cell research.

Thus, there has been described a relatively simple cell separator, which permits separation in a sealed, sterile environment and which can readily be assembled and disassembled.

What is claimed is:

1. A cell separator comprising elongated, tubular casing means, said casing means having an open upper end and a closed lower end; elongated, tubular column means for insertion into said casing means; said column means having a closed upper end and an open lower end; said column means including a plurality of separate, interconnectable tubular sections adapted to releasably support filter means between adjacent sections, and flange means on the uppermost section for sealing engagement with the upper end of said casing means; inlet duct means in said closed upper end of said column means for introducing cells in a liquid medium into said column means; and outlet duct means in said casing means beneath the lower end of said column means for discharging liquid from said casing means, whereby said column means can be inserted and removed from said casing means as a unit, and disassembled from the upper or lower end thereof.

2. A cell separator according to claim 1, wherein at least one said casing sections includes an internally threaded lower end for coupling with the upper end of a subjacent section, and an annular recess in said lower end above the internal threads for receiving a portion of said filter means.

3. A cell separator according to claim 2, wherein said filter means is cup-shaped, including a circular base, and an annular side wall for extending into said recess.

4. A cell separator according to claim 1, including ledge means in the open upper end of said casing means; shoulder means on said flange means for seating on said ledge means; and O-ring means on said shoulder means for sealing engagement with said ledge means.

5. A cell separator according to claim 1, including gas inlet means in the closed upper end of said column means, whereby air can be introduced into said column means to facilitate cell separation.

6. A cell separator according to claim 1 including a retaining ring for supporting filter means between adjacent sections, and a sealing ring for providing a seal between said retaining ring and the upper end of a subjacent section of said column means.

7. A cell separator according to claim 2 including a retaining ring for supporting filter means between adjacent sections, and a sealing ring for providing a seal between said retaining ring and the upper end of a subjacent section of said column means.

8. A cell separator according to claim 3 including a retaining ring for supporting filter means between adjacent sections, and a sealing ring for providing a seal between said retaining ring and the upper end of a subjacent section of said column means.

* * * * *